United States Patent
Törmälä et al.

[11] Patent Number: 6,113,640
[45] Date of Patent: Sep. 5, 2000

[54] RECONSTRUCTIVE BIOABSORBABLE JOINT PROSTHESIS

[75] Inventors: Pertti Törmälä; Senja Paasimaa; Matti Lehto, all of Tampere; Mauri Lehtimäki, Kangasala, all of Finland

[73] Assignee: Bionx Implants Oy, Tampere, Finland

[21] Appl. No.: 08/873,174

[22] Filed: Jun. 11, 1997

[51] Int. Cl.[7] .................................................. A61F 2/30
[52] U.S. Cl. .............................. 623/18; 623/13; 623/17; 606/151
[58] Field of Search .............................. 623/13, 17, 18; 600/37; 606/151

[56] References Cited

U.S. PATENT DOCUMENTS

| | | |
|---|---|---|
| 3,593,342 | 7/1971 | Neibauer et al. . |
| 3,867,728 | 2/1975 | Stubstad et al. .......................... 623/17 |
| 4,313,232 | 2/1982 | Habal et al. . |
| 4,634,445 | 1/1987 | Helal . |
| 4,655,777 | 4/1987 | Dunn et al. . |
| 4,743,257 | 5/1988 | Tormala et al. . |
| 4,873,976 | 10/1989 | Schreiber . |
| 4,884,572 | 12/1989 | Bays et al. . |
| 4,895,141 | 1/1990 | Koeneman et al. . |
| 4,898,186 | 2/1990 | Ikada et al. . |
| 4,968,317 | 11/1990 | Tormala et al. . |
| 4,976,715 | 12/1990 | Bays et al. . |
| 5,059,206 | 10/1991 | Winters . |
| 5,084,051 | 1/1992 | Tormala et al. . |
| 5,092,896 | 3/1992 | Meuli et al. . |
| 5,108,443 | 4/1992 | Branemark . |
| 5,201,766 | 4/1993 | Georgette . |
| 5,207,712 | 5/1993 | Cohen . |
| 5,236,431 | 8/1993 | Gogolewski . |
| 5,261,914 | 11/1993 | Warren . |
| 5,374,268 | 12/1994 | Sander . |
| 5,376,118 | 12/1994 | Kaplan et al. .......................... 623/13 |
| 5,425,766 | 6/1995 | Bowald .......................... 623/13 |
| 5,480,447 | 1/1996 | Skiba . |
| 5,507,823 | 4/1996 | Walston et al. . |
| 5,514,181 | 5/1996 | Light et al. .......................... 623/13 |
| 5,534,033 | 7/1996 | Simpson . |
| 5,549,676 | 8/1996 | Johnson .......................... 623/18 |
| 5,562,704 | 10/1996 | Tamminmaki et al. . |
| 5,569,252 | 10/1996 | Justin et al. . |
| 5,683,466 | 11/1997 | Vitale . |
| 5,702,472 | 12/1997 | Huebner . |
| 6,008,430 | 12/1999 | White .......................... 623/18 |

FOREIGN PATENT DOCUMENTS

| | | |
|---|---|---|
| 0 146 398 A2 | 6/1985 | European Pat. Off. . |
| 0 454 645 | 10/1991 | European Pat. Off. . |
| 0 526 682 | 2/1993 | European Pat. Off. . |
| 0 423 155 B1 | 11/1994 | European Pat. Off. . |

(List continued on next page.)

OTHER PUBLICATIONS

Sasserath et al., Acta Stomatologica, Belgica 88, No. 1 (1991), pp. 5–11 (See English language Summary on p. 10).
Ashammakhi et al., Strength retention of self–reinforced polyglycolide membrane: an experimental study, Biomaterials 16 (1995), pp. 135–138.

(List continued on next page.)

*Primary Examiner*—Paul B. Prebilic
*Attorney, Agent, or Firm*—Kenyon & Kenyon

[57] ABSTRACT

A cylindrical, fibrous, porous joint spacer is provided, having excellent properties, flexibility of formation, and operability, which is intended to be implanted as a prosthesis between bones to be joined together. The joint spacer of the present invention can be formed from a strip of fabric, which is comprised of bioabsorbable fibers and made by a knitting, weaving, non-woven or other technique. The fabric is typically relatively narrow (e.g. 1 to 10 mm wide) and thin (e.g. 0.1 to 1.0 mm thick), depending on the intended application of the prosthetic device to be formed from the fabric. The joint spacer of the present invention is made by wrapping said fabric to yield a cylindrical body; and fixing the free end of the fabric to the surface of the cylindrical body so formed. The joint spacer of the present invention can be implanted in conjunction with one or more fixation parts, to hold the joint spacer in place between the bones to be joined.

16 Claims, 5 Drawing Sheets

FOREIGN PATENT DOCUMENTS

| | | |
|---|---|---|
| 645 149 A1 | 3/1995 | European Pat. Off. . |
| 0 773 008 | 5/1997 | European Pat. Off. . |
| 80605 | 3/1990 | Finland . |
| 2 458 275 | 1/1981 | France . |
| 2 712 486 | 5/1995 | France . |
| WO 85/01210 | 3/1985 | WIPO . |
| WO 88 05312 | 7/1988 | WIPO . |
| WO 89/03663 A1 | 5/1989 | WIPO . |
| WO 90 12550 | 11/1990 | WIPO . |
| WO 91/16014 A1 | 10/1991 | WIPO . |
| WO 93 14705 | 8/1993 | WIPO . |
| WO 94/13228 | 6/1994 | WIPO . |
| WO 95 22359 | 8/1995 | WIPO . |
| WO 96/21628 | 7/1996 | WIPO . |
| WO 96 24310 | 8/1996 | WIPO . |
| WO 96/41596 | 12/1996 | WIPO . |

OTHER PUBLICATIONS

Vainionpaa et al., Surgical Applications of Biodegradable Polymers in Human Tissues, Prog. Polym. Sci. 14 (1989), pp. 679–716.

N.A.Palmeri et al., The Development and Testing of Arthroscopic Meniscal Staple, Arthroscopy, vol. 5, No. 2, 1989, p. 156.

Cato T. Laurencin et al., Use of Polyphosphazenes for Skeletical Tissue Regeneration, Journal of Biomedical Materials Research, vol. 27, pp. 963–973 (1993).

Medical Data International, Inc., Orthopedic and Musculoskeletal Markets: Biotechnology and Tissue Engineering, Feb. 1997 at ES 1–18 and 1–28.

PCT International Search Report for PCT/FI 96/00351 (4 pages).

Search Report for Finnish Patent Application No. 952884.

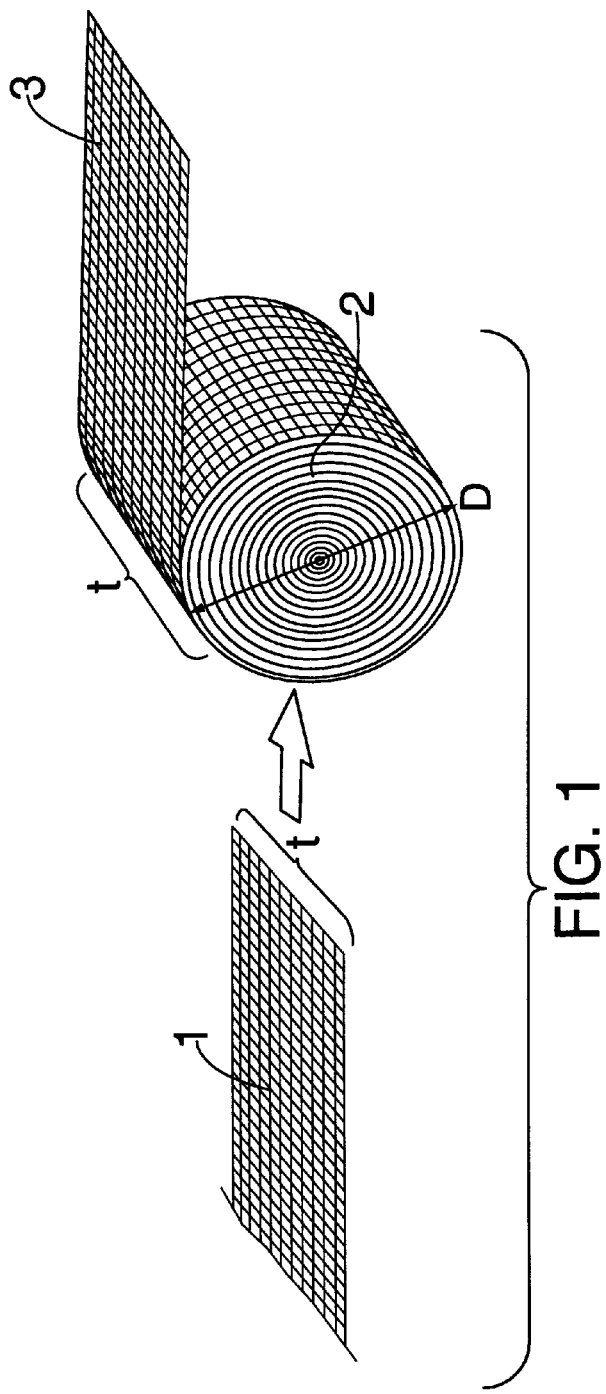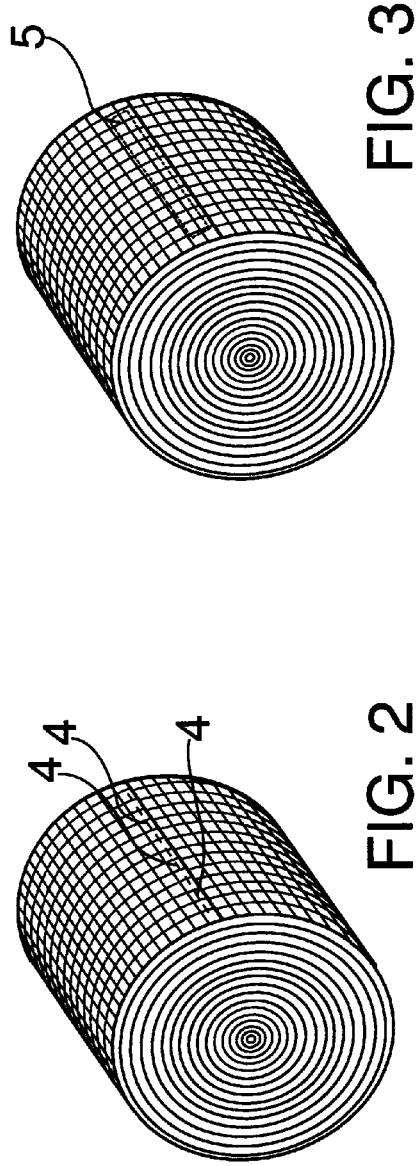
FIG. 1
FIG. 2
FIG. 3

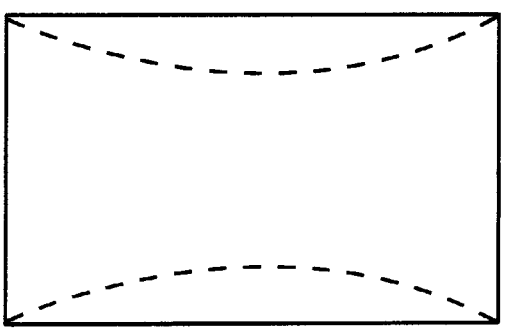
FIG. 5
FIG. 6

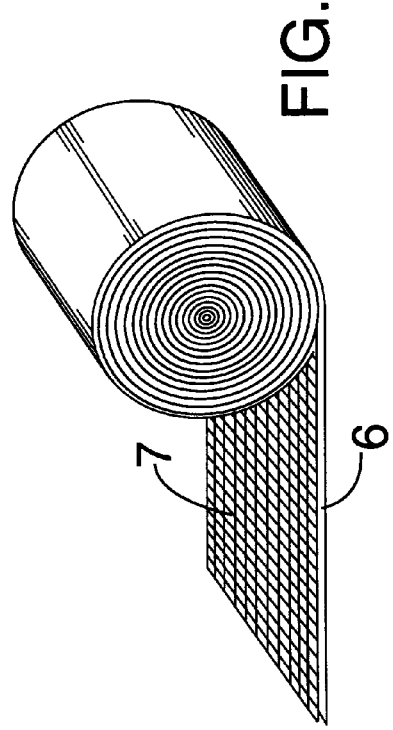
FIG. 7

RECONSTRUCTIVE BIOABSORBABLE JOINT PROSTHESIS

FIELD OF THE INVENTION

The present invention relates to a biologically active joint prosthesis, and a method of its manufacture.

BACKGROUND OF THE INVENTION

It is known in the art to use synthetic, elastic, joint implants made of non-biodegradable plastics to replace damaged tissue joints, particularly joints connecting between small bones in the hands and feet. A typical biostable elastic joint prosthesis is composed of a spacer portion, which is positioned between the bones to be joined, and two elongated fixation portions, which are anchored in the bones to be joined. Such an artificial joint is available, for example, from Dow Corning, S.A., Valbourne Cedex, France, under the trade name Silastic®. The Silastic® implant is made of an elastomer material.

However, the use of joint prostheses manufactured of biostable polymers, polymer mixtures and elastomers can cause problems for the patient. One such problem with biostable joint prostheses is that the operated limb can only withstand a set amount of strain following the operation. For example, when a Silastic® joint prosthesis is used to replace a finger joint, the operated hand cannot bear a strain of more than 5 kg-force, and over-straining may lead to breaking or wearing of the implant forming the joint prosthesis. Another problem of such biostable joint prosthesis is that loose particles may be released from the joint prosthesis, due to wearing, fatigue and/or corrosion, which particles may cause a chronic inflammation reaction, e.g., a synovitis, and/or osteological changes in the bone. Further, the inflammation reaction may cause tumefaction and pain in the joint, often to a degree which requires removal of the joint prosthesis.

PCT publication WO 96/41596, which is assigned to the assignee of the present application, describes a biodegradable joint prosthesis that is comprised of a spacer part and proximal and distal fixation parts, which are fixed to the bones to be joined. A joint prosthesis in accordance with WO 96/41596 can be implanted in the hand, wrist or foot area to entirely or partially replace a damaged joint. The spacer part of the joint prosthesis of WO 96/41596 keeps the bones to be joined at a desired distance from each other. The joint prosthesis is fixed to the bones by anchoring the proximal and distal fixation parts, respectively, in the two bones to be joined. The strength and ductility values of the fixation parts of the joint prosthesis of WO 96/41596 are chosen to allow bending of the operated joint shortly after implantation.

The spacer part of the joint prosthesis of WO 96/41596 is important to the function of the prosthesis. In order to obtain a desired porosity (typically, a pore size of between 50 μm and 1000 μm), the spacer part of WO 96/41596 is preferably formed of a fibrous, three dimensional, partly porous structure of biodegradable fibers, which fibers have a typical thickness of between 1 and 300 μm. To produce that spacer part, the biodegradable fibers can be woven or knit or formed into a non-woven fabric and, then, folded or wrapped into a three-dimensional, pillow-like, porous structure. The spacer part of WO 96/41596 can also be produced from: (I) a continuous fiber blank using three dimensional weaving, knitting or twisting techniques, wherein a desired length of the continuous fiber blank is cut for each spacer part, (ii) biodegradable fibers which are cut into desired lengths and are bound together using a biodegradable binding blank; or (iii) a biodegradable, continuous, polymer blank which is treated to produce open porosity therein.

The shape of the spacer part of WO 96/41596 preferably corresponds to the space between the bones to be joined by the joint prosthesis. Accordingly, that spacer part may have the shape of a pillow, a cylinder, an ellipsoid, (flattened) ball, cubic or rectangular prism, or other three dimensional structure which, as well as possible, fills the space constructed for the spacer part between the bones to be joined. The spacer part of WO 96/41596 is advantageously elastic, and it may not contain any sharp and/or hard edges or angles which could cause mechanical irritation of the surrounding tissue.

SUMMARY OF THE INVENTION

According to the present invention, a cylindrical, fibrous, porous joint spacer is provided, having excellent properties, flexibility of formation, and operability, which is intended to be implanted as a prosthesis between bones to be joined together. The joint spacer of the present invention can be formed from a strip of fabric, which is comprised of bioabsorbable fibers and made by a knitting, weaving, non-woven or other technique. The fabric is typically relatively narrow e.g. 1 to 10 mm wide) and thin (e.g. 0.1 to 1.0 mm thick), depending on the intended application of the prosthetic device to be formed from the fabric. Under the present invention, the joint spacer is made by wrapping said fabric to yield a cylindrical body, and fixing the free end of the fabric to the surface of the cylindrical body so formed. The joint spacer of the present invention can be implanted in conjunction with one or more fixation parts, to hold the joint spacer in place between the bones to be joined.

BRIEF DESCRIPTION OF THE DRAWINGS

FIG. 1 illustrates the wrapping of a fabric to form a cylindrical body.

FIG. 2 illustrates the fixing, by sewing, of the end of the fabric to the surface of the cylindrical body FIG. 3 illustrates the fixing, by glueing, of the end of the fabric to the surface of the cylindrical body.

FIG. 5 illustrates a fabric that can be used in the present invention, wherein the fabric is made of curled or spirally bent fibers.

FIG. 6 illustrates a cylindrical body, wherein the cylindrical body is thinner at its center and thicker at its outer edges.

FIG. 7 illustrates the wrapping of a fabric with a glueing film to form a cylindrical body.

DETAILED DESCRIPTION OF THE PREFERRED EMBODIMENTS

Figure 4A:
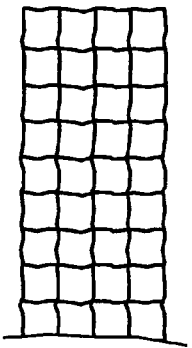
FIG. 4A illustrates a view of a fabric that can be used in the present invention wherein the outer layers are composed of fibers of smaller diameters.
Figure 4B:
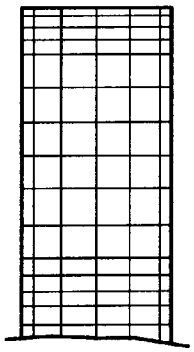
FIG. 4B illustrates a view of a fabric that can be used in the present invention wherein the ends of the fabric are more tightly wound and the center of the fabric.
Figure 4D:
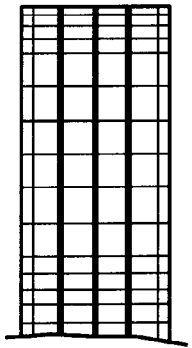
FIG. 4D illustrates a view of a fabric that can be used in the present invention wherein the inner layers are composed of fibers of smaller diameters, wherein each fabric shown in FIGS. 4A, 4B, 4C and 4D has a different thickness and/or tightness of its fibers.
Figure 4C:
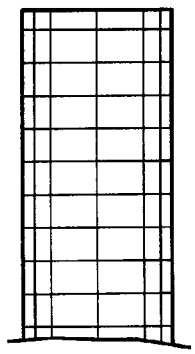
FIG. 4C illustrates a view of a fabric that can be used in the present invention wherein the inner layers are tightly wound.

The present invention relates to an implantable, cylindrical, fibrous prosthesis, having improved properties and functional characteristics, and a method for its manufacture.

As shown by FIG. 1, the joint spacer of the present invention is manufactured from a fibrous fabric 1 that is wrapped to form a cylindrical body 2. The size of the cylindrical body so formed is characterized by its diameter "D" and its thickness "t", as illustrated in FIG. 1. According to FIGS. 1, 2, and 3, the free end of the fabric 3 is fixed to the surface of the cylindrical body, e.g., by sewing with a bioabsorbable suture 4, or by glueing with a bioabsorbable polymer melt or solution 5.

Manufacturing the cylindrical body 2 by wrapping the fabric yields several advantages over the prior art. The diameter D of the cylindrical body can be varied easily and conveniently by varying the length of the fabric used to form the cylindrical body. Moreover, the surgeon can easily make D smaller in the operation room, if necessary, by opening the fixation (4 or 5) of the cylindrical body, unwrapping the fabric to the desired point, cutting the unwrapped part away, and attaching the new free end of the fabric onto the cylindrical body. Likewise, the thickness t of the cylindrical body 2 can be varied easily by selecting fabrics having different widths t', as shown in FIG. 1.

The porosity of the cylindrical body 2 also can be advantageously varied in several ways. For example, the porosity of the fabric 1 can be adjusted by varying the textile structure of the fabric. The pore size and distribution of the fabric 1 also can be adjusted by varying the thickness of the fibers used to make the fabric, i.e., by using thinner (e.g., 0.1–10 μm) fibers, thicker fibers (e.g., 10–500 μm) or mixtures thereof in the fabric. The porosity of the fabric 1 (and the cylindrical body 2) also can be adjusted by varying the distribution and/or the diameter of the fibers used to make the fabric. Shown schematically in FIG. 4A, FIG. 4B, FIG. 4C and FIG. 4D are examples of some typical fabrics for use in the present invention, having various distributions and/or diameters of fibers. In addition to those illustrated in FIG. 4A, FIG. 4B, FIG. 4C, and FIG. 4D, numerous other fiber thicknesses and distributions in the fabric are possible under the present invention. By varying the thickness and/or distribution and/or orientation of the fibers, and/or varying the knitting, weaving or non-woven technique used to make the fabric from such fibers, joint spacers can be prepared according to various specifications regarding load bearing properties, frictional properties and tissue growth properties.

As shown in FIG. 5, the fibers can be curled or twisted helically before the manufacturing of the fabric 1. When such a fabric is wrapped, the resultant cylindrical body 2 is especially porous and elastic. The porosity of the cylindrical body 2 also can be varied by adjusting the tension applied to the fabric during the wrapping procedure. If low tension is used, the wrapped cylindrical body is loose and soft, and the thickness t of the cylindrical body can be almost the same as the width t' of the fabric. If high tension is used during the wrapping procedure, making the fabric tighter, harder and less porous, the thickness t of the resultant cylindrical body can be made smaller than the width t' of the fabric. Moreover, by varying the tension on the fabric during the wrapping procedure, a cylindrical body can be produced that has a varied thickness and porosity. As an example, when high tension is used at the beginning of the wrapping procedure and that tension is reduced progressively during the wrapping, a cylindrical body is produced having a middle section of high density and low thickness, as is illustrated in FIG. 6.

The fabric used to make the joint spacer of the present invention can be manufactured using fibers of a biodegradable polymer, co-polymer, polymer mixture or composition, or by combining various biodegradable polymer substances. When fibers of various biodegradable polymers are combined to make the fabric under the present invention, a joint spacer can be constructed that will degrade in the tissue in a non-uniform manner, as the various fibers making up the fabric may have different degradation rates in tissue. Alternatively, such non-uniform degradation of the joint spacer in tissue can be achieved under the invention by coating the fabric with a biodegradable material having a different degradation rate in tissue than the polymer or polymers used to make the fabric.

In the medical, technical and patent literature, a multitude of biodegradable polymers have been identified that are suitable as raw materials for making joint prostheses in accordance with the present invention. These include, for example, biodegradable aliphatic polyesters (c., e.g., Vainionpää, S. Rokkanen, P., and Törmälä, P. in Progr. *Polym. Sci.*, 14 (1989) pp. 679–716; U.S. Pat. Nos. 4,743,257, 5,084,051, U.S. Pat. No. 4,968,317; EPO Application No. 0423155; and PCT application No. PCT/FI93/00014); and polyester amides, polyorthoesters, polyanhydrides and polyphosphazenes (cf., e.g., C. T. Laurensin et al., *J. Bigmed Mater. Res.* 27 (1993), pp. 963–973).

When located in a joint cavity, the joint spacer of the present invention will be covered and/or filled relatively rapidly with connective tissue. During that biodegradation process, the joint spacer is replaced by a biological, fibrous tissue. As a result, a new, biological, elastic fibrous tissue joint is obtained, which allows moving of the joint bones by the surrounding muscles. As the new joint is formed during the degradation process of the joint spacer, no foreign particles are released that are chronically harmful to the patient's system, as can be the case with the so-called biostable joint prostheses. Thus, the joint spacer of the present invention entirely eliminates the risks of such chronic complications caused by loose foreign particles which are possible when using biostable joint prostheses To permit tissue growth within the joint spacer after its implantation, the cylindrical body of the present invention is advantageously porous, with the pore size varying between, e.g., 50 μm and 1000 μm. The pore size of the cylindrical body can be varied, as illustrated above, in accordance with the desired mechanical strength of the prosthesis and distance between the bones to be joined.

Figure 8:
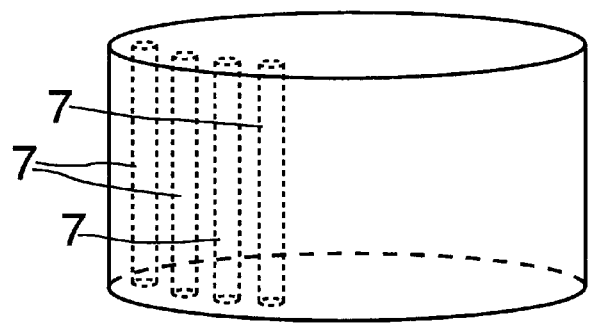
FIG. 8 illustrates a porous cylindrical body, wherein the cylindrical body has longitudinal vertical pores

In one embodiment of the present invention, the wrapped fabric layers of the cylindrical body are glued together, either by coating the surface of the fabric with another bioabsorbable polymer having a lower melting temperature than the fabric prior to wrapping the fabric, or by using a glueing bioabsorbable film 6 which is wrapped with the fabric 1, as shown in FIG. 7. The glueing of the fabric also can be accomplished using a solution of another bioabsorbable polymer. By using heat and/or pressure, the fabric coating or the glueing bioabsorbable film can be softened and/or melted to bind the wrapped fabric and form a solid cylindrical body. Especially when using the glueing bioabsorbable film as above, it is possible to create oriented porosity and/or channels 7 in the perpendicular direction in relation to the even surfaces of the cylindrical body, as is illustrated schematically in FIG. 8. Such oriented pores and/or channels are advantageous where guided tissue regeneration (i.e., tissue growth directed in specific directions) is desired.

Under the present invention, the stiffness, flexibility, surface quality and porosity of the cylindrical body can be controlled by annealing the cylindrical body at elevated temperatures (typically, at a temperature $T>T_g$, where $T_g$ is the glass transition temperature a fiber component of the cylindrical body), optimally in a suitable mold and under mechanical pressure. Annealing and the simultaneous mechanical pressure make the cylindrical body stiffer and, if the treatment is done in a mold, the form of the cylindrical body can be changed permanently, e.g., the circular geometry of the cylindrical body can be flattened or its even surfaces can be made curved.

Figure 9A:
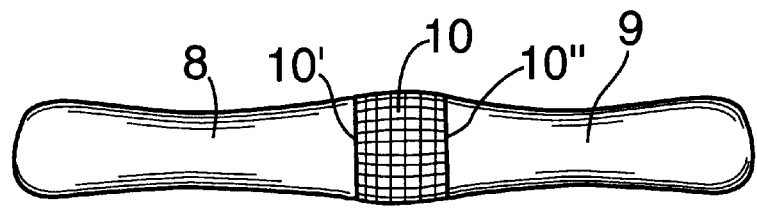
FIG. 9A illustrates an arrangement between bones and a cylindrical body where the joint surface of both bones has been removed.
Figure 9B:
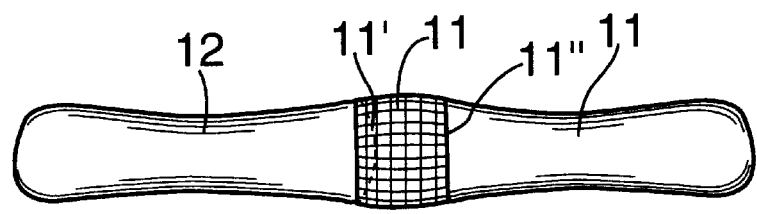
FIG. 9B illustrates an arrangement between bones and a cylindrical body where the joint surface is removed only from one bone.
Figure 9C:
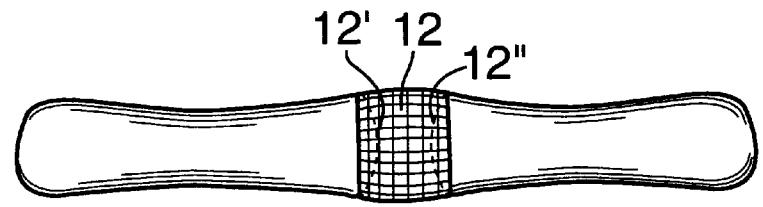
FIG. 9C illustrates an arrangement between bones and a cylindrical body where surfaces of the cylindrical body are concave.

The joint spacer of the present invention performs surprisingly well after implantation, whether one or both of the bones to be joined have had the joint surface removed. FIG. 9A shows as a cross-section of joint surfaces of two finger or toe bones, 8 and 9, where the joint surface of both bones has been removed and the joint space is filled with a cylindrical body 10 having planar surfaces 10' and 10", FIG. 9B shows an embodiment where the joint surface is removed only from one bone 11 and not removed from the other bone 12 to be joined. To accommodate this situation, one surface 11' of the implanted cylindrical body 11 can be made concave and the other surface 11" can be made planar. FIG. 9C illustrates a case where both surfaces, 12' and 12", of the cylindrical body 12 are concave to fit the convex joint surfaces of the two bones to be joined.

The joint spacer (cylindrical body) of the present invention also can be used as in combination with different types of fixation parts (e.g., one or more pins, screws, bolts or rods, alone or in combination) arranged to fix the joint spacer to the bones to be joined, as is described in WO 96/41596 with regard to the spacer part and fixation parts of that reference. The fixation parts of the joint prosthesis in accordance with the present invention are characterized in that they are joined to the joint spacer to form a fixed and integrated entity, in a manner that the fixation parts and the joint spacer together form a flexible joint prosthesis. By way of the fixation parts, the joint spacer is kept between the bones to be joined, wherein by means of muscular power it is possible to bend the bones to be joined in relation to each other.

In accordance with the present invention, the fixation parts can be manufactured of biodegradable polymer, polymer mixture or composition, by using melt molding methods, such as injection molding or extrusion, or they can be formed mechanically from a polymer blank to achieve the desired form. Self-reinforced biodegradable compositions are particularly advantageous compositions for use as raw materials in making the fixation parts in accordance with the present invention. Such compositions are known in the art and have been described in publications such as U.S. Pat. No. 4,743,257 and application No. WO 88/05312. Other biodegradable compositions may also be used to reinforce the fixation parts in accordance with the present invention, wherein the fixation part is reinforced by fibers, cut fibers, filaments or structures constructed thereof, such as braidings, threads, strings, non-woven structures, cloths, knittings etc., which reinforcement also is made of a biodegradable polymer, copolymer or polymer mixture. Biodegradable compositions for making such reinforcements for the fixation part are known in the art, and many such polymers are identified in the references cited herein. The fixation part of the present invention can also be reinforced with fibers made of biodegradable ceramic material, such as bioglass or calcium phosphate (cf., e.g., Vainionpää, S., Rokkanen, P. and TörmäJä, P. in *Prog. Polym. Sci.* 14 (1989), pp, 679–716).

Fixation parts in accordance with the invention, which are reinforced by biodegradable organic and/or inorganic fibers or structures constructed thereof, can be manufactured by various methods known in plastic technology, e.g., by binding the reinforced structures, at least partially, to each other by bioabsorbable polymer, copolymer or polymer mixture (matrix), under conditions in which the matrix is in solution (or melted form) and a sufficiently homogeneous composition is formed from the matrix and the reinforcing agent. Injection molding, extrusion, winding, compression molding and other methods all can be used when combining the reinforcing fibers or the like and the matrix, and when forming that combination into prefabricates and/or implants. If desired, the fixation parts of the present invention can be porous in a similar manner to the joint spacer, wherein tissue growth takes place in the open porosity of the fixation part from the surrounding tissue and, as a result, the fixation part is rapidly locked into its place.

The implants (joint spacer and fixation part) of the present invention may also include various additives to facilitate the processability of the material (for example stabilizers, antioxidants, or softening agents) or to change its properties (for example softening agents or ceramic chemicals in powder form or biostable fibers, such a carbon fibers) or to facilitate its use (e.g., coloring agents). The fixation part of the present invention also can be constructed of the patient's own fibrous tissue, such as tendon or ligament tissues, by manipulating a sufficiently long part of a tendon or ligament extending from one bone to be joined to the other such bone, in such a manner that the joint spacer is placed between the bones and the tendon or ligament penetrates the spacer part.

According to one advantageous embodiment of the invention, the joint spacer and/or fixation part contain a bioactive agent or agents, such as antibiotics, chemotherapeutic agents, agents accelerating wound healing, agents inducing the forming of cartilage collagen, growth hormones, anticoagulant (such as heparin), etc. Bioactive mediums of this type are particularly advantageous in clinical use, because, in addition to the mechanic effect, they have biochemical effects (for example, accelerating the growth of fibrous and/or cartilage tissue), medical and other effects in human tissues.

The fixation part of the present invention can have a rigid or flexible structure. A rigid fixation part typically comprises a rod, bar, screw or pin, which at its stem is connected to the joint spacer and whose point is inside the bone to be joined. A profiling (such as a screw thread, various scales or steps) on the surface of a fixation part of this type facilitates the locking of the fixation part into the hole made inside the bone. An elastic fixation part can be comprised of, for example, a cloth ("a veil") that is attached to or part of the joint spacer, and which is fixed (with small absorbable pins or a suture) on the surface of the bone to be joined. Such an elastic fixation part can also be comprised of one or more loops of absorbing suture which are used for fixing the joint spacer to the bone to be joined.

Figure 10A:
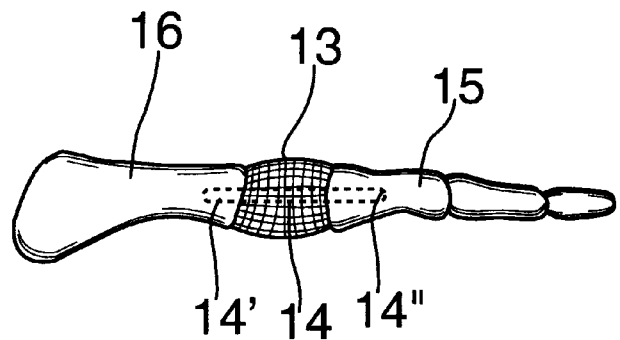
FIG. 10A illustrates a joint prosthesis comprised of a cylindrical body and fixation pin, as seen from the side, wherein the joint provided with a joint prosthesis is straight.
Figure 10B:
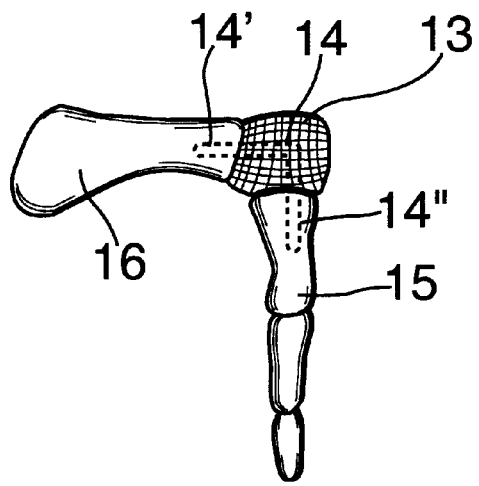
FIG. 10B illustrates a joint prosthesis comprised of a cylindrical body and fixation pin, as seen from the side, wherein the joint provided with a joint prosthesis is bent.
Figure 10C:
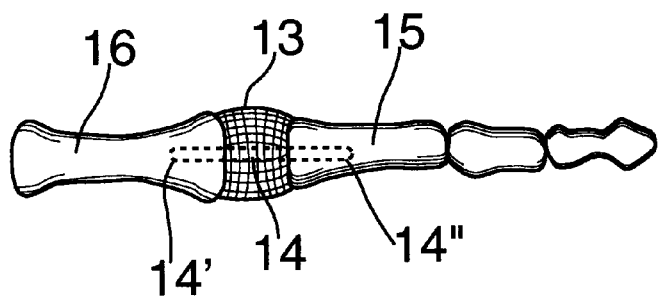
FIG. 10C illustrates a joint prosthesis comprised of a cylindrical body and fixation pin, as seen from above, wherein the joint provided with a joint prosthesis is straight.

FIGS. 10A, 10B and 10C illustrate schematic views of one application of the joint prosthesis according to the invention, to be used for joining together small bones (such as hand and feet bones).

FIG. 10A is a schematic figure of the bones 15 and 16, as seen from the side, i.e., from a position parallel to the bending direction of the joint, wherein the joint provided with a joint prosthesis is straight.

FIG. 10B is a schematic figure of the bones 15 and 16, as seen from the side, i.e. from a position parallel to the bending direction of the joint, wherein the joint provided with a joint prosthesis is bent.

FIG. 10C is a schematic figure of the bones 15 and 16, as seen from above, i.e., from a position perpendicular to the bending direction of the joint, the joint provided with a joint prosthesis is straight.

As shown in FIGS. 10A, 10B and 10C, a rod-like fixation part 14 traverses a cylindrical body 14, and the ends 14' and 14" of the fixation part are located inside of bones 15 and 16. The present invention can be implanted in numerous other configurations of fixation parts and joint spacers (spacer parts), as is known in the art and shown, for example, in FIGS. 1–5 of WO 96/41596.

Figure 11A:
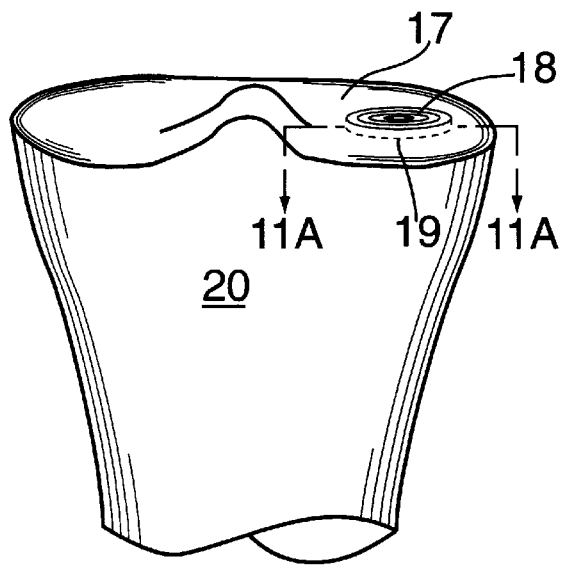
FIGS. 11A and 11B illustrate a cylindrical body as a partial prosthesis on the synovial cartilage surface, located at the proximal end of a tibia.
Figure 11B:
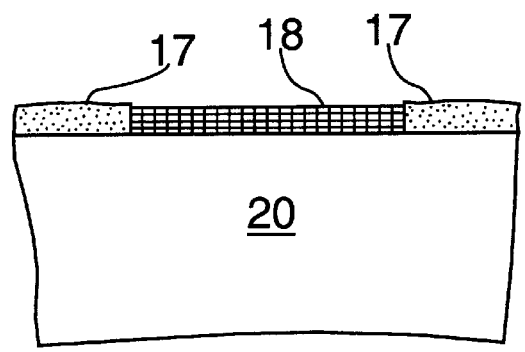

As shown in FIG. 11A, moreover, the cylindrical body (joint spacer) of the invention can be used as a partial prosthesis on a synovial joint surface 17. As is seen in the cross-sectional plane a—a in FIG. 11B, the flat cylindrical body 18 is located in a cavity 19 in the cartilage surface 17, on the surface of the bone 20. The porous, fibrous cylindrical body 18 induces the formation of new cartilage into the cavity 19 during bioabsorption of the cylindrical body and its replacement with newly grown tissue. As a result of this process, a new cartilage surface is created in the damaged cavity 19. In one advantageous embodiment, the cylindrical body 18 is loaded with chondrocytes or some similar type of cells before implantation. In tissue engineering it is known that several types of cells can be taken from the patient, multiplied under cell culture conditions, loaded into a porous bioabsorbable joint spacer (cylindrical body) and implanted into the patient to facilitate the healing of tissue trauma or deficiency.

Figure 12:
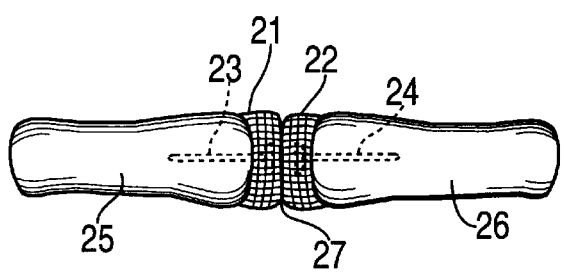
FIG. 12 illustrates a prosthesis comprising two cylindrical bodies and two fixation parts, wherein a cavity is formed between the two cylindrical bodies.

In another advantageous embodiment of the present invention, the prosthesis comprises two cylindrical bodies, which can be located parallel to one another in the joint cavity. In such a configuration, a vertical cavity is left between the cylindrical bodies, simulating the synovial joint cavity. As shown in FIG. 12, cylindrical bodies 21 and 22 are fixed to bones 25 and 26 with nail-like fixation parts 23 and 24, so that a synovial cavity-like space 27 is left between cylindrical bodies 21 and 22. When the patient moves the joint following such an implantation, the cylindrical bodies 21 and 22 glide in relation to each other and the synovial cavity-like space can remain inside the growing fibrous joint.

In another advantageous embodiment of the invention shown in FIG. 12, the contacting surfaces of cylindrical bodies 21 and 22, which contacting surfaces form the walls of the cavity 27, can be coated with hyaline cartilage cells and/or with growth factors or other bioactive substances (or with another bioabsorbable polymer that releases growth factors), promoting the growth of hyaline cartilage or the formation of a cartilage layer on the cavity surfaces of the growing joint. In addition, as shown in FIG. 12, the surfaces of the cylindrical bodies 21 and 22 that are in contact with the bones 25 and 26 can be coated with bone morphogenic proteins (BMP), or with another BMP releasing bioabsorbable polymer to facilitate ossification of each cylindrical body 21 and 22 into the corresponding bone.

Figure 13:
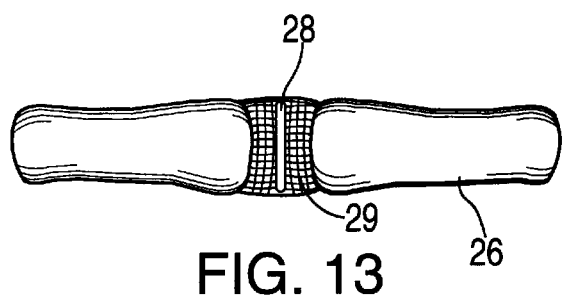
FIG. 13 illustrates a cylindrical body implanted between two bones, wherein the cylindrical body contains a circular fissure to simulate a synovial cavity.

Another manner of simulating a synovial cavity under the present invention is illustrated by FIG. 13. As shown in that figure, a flat hole or circular fissure 28 is located inside the cylindrical body 29.

What is claimed is:

1. A prosthesis for implantation between bones to be joined, comprising a porous joint spacer made by wrapping a bioabsorbable fabric into a cylindrical body and a bioabsorbable fixation part, wherein said fixation part is capable of fixing said cylindrical body to a bone.

2. A prosthesis as set forth in claim 1, further characterized in that the porosity of the joint spacer is about 50 µm to 1000 µm.

3. A prosthesis as set forth in claim 1, further characterized in that the porous joint spacer is made by wrapping into the cylindrical body a bioabsorbable film that binds with the bioabsorbable fabric.

4. A prosthesis as set forth in claim 1, farther characterized in that the bioabsorbable fabric is comprised of at least two compounds having different degradation rates in tissue than each other.

5. A prosthesis as set forth in claim 1, further characterized in that the bioabsorbable fabric is coated with a material having a different degradation rate in tissue than the bioabsorbable fabric.

6. A prosthesis as set forth in claim 1, further characterized in that the bioabsorbable fabric is made from two or more biodegradable fibers having different degradation rates in tissue than each other.

7. A prosthesis as set forth in claim 1, further characterized in that the fabric is made from biodegradable fibers having a thickness of about 1 to 300 µm.

8. A prosthesis as set forth in claim 1, further characterized in that the fixation part comprises at least one pin, screw, bolt or rod.

9. A prosthesis as set forth in claim 1, further characterized in that the fixation part is comprised of at least one thread, braid or cloth.

10. A prosthesis as set forth in claim 1, further characterized in that the fixation part is comprised of part of the cylindrical body.

11. A prosthesis as set forth in claim 1, further characterized in that the fixation part is comprised of a bioabsorbable suture.

12. A prosthesis as set forth in claim 1, further characterized in that the fixation part is comprised of tissue.

13. A prosthesis for implantation between bones to be joined, comprising: a first porous joint spacer made by wrapping a bioabsorbable fabric into a cylindrical body and a first bioabsorbable fixation part capable of attaching said first joint spacer to a bone; and a second porous joint spacer made by wrapping a bioabsorbable fabric into a cylindrical body and a second bioabsorbable fixation part capable of attaching said second joint spacer to a bone, wherein the first porous joint spacer and the second porous joint spacer are configured to form a cavity.

14. A method of forming a prosthesis for implantation between bones to be joined, comprising the steps of:

a. cutting a strip of a bioabsorbable fabric to a desired length;

b. wrapping the bioabsorbable fabric into a cylindrical body;

c. attaching the free end of the bioabsorbable fabric to the cylindrical body; and d. attaching a bioabsorbable fixation part to said cylindrical body.

15. A prosthesis as set forth in claim 1, further characterized in that at least one surface of the cylindrical body is concave.

16. A method of forming a prosthesis for implantation between bones to be joined as set forth in claim 14, further comprising the step of annealing the cylindrical body.

\* \* \* \* \*